United States Patent [19]

Haas et al.

[11] 4,057,573

[45] Nov. 8, 1977

[54] HYDROAROMATIC COMPOUNDS

[75] Inventors: Georges Haas; Alberto Rossi, both of Oberwil, Switzerland

[73] Assignee: Ciba-Geigy Corporation, Ardsley, N.Y.

[21] Appl. No.: 548,956

[22] Filed: Feb. 11, 1975

[30] Foreign Application Priority Data

Feb. 14, 1974 Switzerland .......................... 2094/74

[51] Int. Cl.$^2$ ............................................. C07C 69/76
[52] U.S. Cl. .................................. 560/52; 260/297 B; 260/332.2 R; 260/520 D; 260/559 R; 560/139; 560/56; 560/8; 560/51; 260/410.5
[58] Field of Search ................ 260/473 R, 473 F, 469

[56] References Cited
U.S. PATENT DOCUMENTS 3,940,434  2/1976  Haas et al. .................... 260/473 F Primary Examiner—Paul J. Killos
Attorney, Agent, or Firm—Theodor O. Groeger

[57] ABSTRACT

Compounds of the general formula I

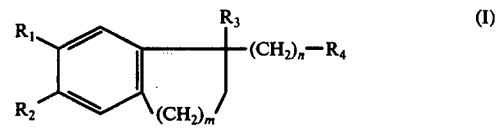

wherein one of the two radicals $R_1$ and $R_2$ denotes the acyl radical of a carboxylic acid of aromatic character and the other denotes hydrogen or optionally esterified or etherified hydroxyl, $R_3$ denotes hydrogen, alkyl or hydroxyalkyl, $R_4$ denotes optionally esterified or amidised carboxyl, $m$ denotes 1 or 2 and $n$ denotes 0 or 1, in the free form or in the form of their salts are useful as antiphlogistics, mild analgesics, antipyretics and as antirheumatic agents.

11 Claims, No Drawings

HYDROAROMATIC COMPOUNDS

The invention relates to new hydroaromatic compounds of the general formula I

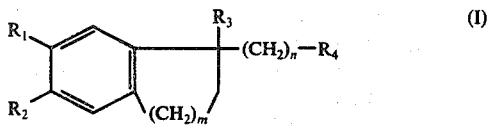

wherein one of the two radicals $R_1$ and $R_2$ denotes the acyl radical of a carboxylic acid of aromatic character and the other denotes hydrogen or optionally esterified or etherified hydroxyl, $R_3$ denotes hydrogen, alkyl or hydroxyalkyl, $R_4$ denotes optionally esterified or amidised carboxyl, $m$ denotes 1 or 2 and $n$ denotes 0 or 1, in the free form or in the form of their salts, processes for the manufacture of these compounds, pharmaceutical preparations containing these compounds, and the use of these preparations.

The acyl radical of a carboxylic acid of aromatic character, $R_1$ or $R_2$, is, for example, a radical of the formula R—CO—, wherein R denotes a radical of aromatic character bonded via a carbon atom and such a radical is to be understood as an aromatic radical which is optionally substituted and optionally contains one or more than one hetero-atom. An aromatic radical which optionally contains one or more than one hetero-atom is, for example, a bicyclic, but preferably a monocyclic, aryl or heteroaryl radical with 5 or 6 ring members, a heteroaryl radical preferably containing one heteroatom, such as nitrogen, oxygen or sulphur. Substituents of R which should be mentioned in particular are lower alkyl, such as methyl, lower alkoxy, such as methoxy or ethoxy, halogen, such as chlorine, bromine or fluorine, and/or trifluoromethyl. Accordingly, the preferred acyl radical of aromatic character is in particular thenoyl, pyridoyl or especially benzoyl, which are optionally polysubstituted or, above all, monosubstituted, by lower alkyl, for example methyl, lower alkoxy, for example methoxy, halogen, for example chlorine, bromine or fluorine, or trifluoromethyl, but are preferably unsubstituted.

Alkyl is, for example, straight-chain or branched lower alkyl, bonded in any desired position, with 1–7, especially 1–4, carbon atoms, such as, for example, straight-chain or branched heptyl, hexyl or pentyl bonded in any desired position, and also, in particular, n-, sec.-, iso- or tert.-butyl, isopropyl, propyl, ethyl and methyl.

Esterified hydroxyl is, for example, a hydroxyl group esterified with a carboxylic acid, preferably with a lower alkane carboxylic acid with up to 7, especially with 2–4, carbon atoms. Examples of esterified hydroxyl $R_1$ to $R_2$ which may be mentioned are caproyloxy, valeroyloxy, iovaleroyloxy and, in particular, butyryloxy, propionyloxy and acetoxy.

Etherified hydroxyl is, for example, lower alkoxy with 1–7, especially with 1–4, carbon atoms, such as, for example, straight-chain or branched heptyloxy, hexyloxy and pentyloxy, as well as n-, sec.-, iso- or tert.-butoxy, isopropoxy, propoxy, ethoxy and methoxy.

Hydroxyalkyl is, for example, hydroxy-lower alkyl, preferably monohydroxy-lower alkyl with 1–7, especially with 1–4, carbon atoms, the hydroxyl group preferably being in the α-position. Hydroxymethyl may be mentioned, above all, as an example of hydroxylalkyl $R_3$.

Esterified carboxyl is, for example, carboxyl esterified with an alcohol of aliphatic character which is optionally substituted and optionally interrupted by one or more heteroatoms, an alcohol of aliphatic character being understood to mean an alcohol of which the carbon atom bonded to the ester-forming hydroxyl group is not part of an aromatic system. An alcohol of aliphatic character which is optionally substituted and optionally interrupted by one or more hetero-atoms is, for example, an alkanol which is optionally substituted by an aryl or heteroaryl radical (which can also be substituted by lower alkoxy, halogen and/or trifluoromethyl) or by lower alkoxy or hydroxyl.

Lower alkoxy alkanols are, for example, lower alkoxy lower alkanols which contain 1–7, especially 1–4, carbon atoms in the lower alkyl part and 2–4, especially 2, carbon atoms in the lower alkylene part. Ethoxyethanol and methoxyethanol may be mentioned as examples.

Aralkanols which are optionally substituted in the aryl part are, for example, α- or β-phenyl-lower alkanols with 1–4, especially 1–3, carbon atoms in the lower alkylene part, which are optionally substituted in the phenyl part by lower alkyl and/or lower alkoxy each with 1–4, carbon atoms, such as methyl, methoxy or ethoxy, halogen, such as fluorine, chlorine or bromine, and/or trifluoromethyl. 2-Phenylpropanols, 1- or 2-phenylethanols, such as phenethyl alcohol, and benzyl alcohols, which are optionally substituted as indicated, may be mentioned as examples.

Heteroaryl alkanols which are optionally substituted in the heteroaryl part are, for example, pyridyl-lower alkanols with 1–4 carbon atoms, preferably 1 carbon atom, in the lower alkyl part, which are optionally substituted in the pyridyl part by lower alkyl or lower alkoxy with 1–4 carbon atoms, such as methyl or methoxy, but are preferably unsubstituted. (2-Pyridyl) methanol, (4-pyridyl)methanol and (2-pyridyl)ethanol may be mentioned as examples.

Hydroxyalkanols are, for example, hydroxy-lower alkanols which contain one or more, preferably 1–3, hydroxyl groups and 2–4, especially 2 or 3, carbon atoms in the lower alkylene part. Propylene glycol, ethylene glycol and glycerol may be mentioned as examples.

Unsubstituted alkanols are, for example, straight-chain or branched lower alkanols with 1–7, especially with 1–4, carbon atoms, such as one of the isomeric heptanols, hexanols, pentanols or butanols, isopropanol, propanol, ethanol or methanol.

Amidised carboxyl contains a primary, secondary or tertiary amino group as the amino group.

Secondary amino groups are, for example, amino groups substituted by a hydroxyl or amino group or by optionally substituted lower alkyl. Substituted lower alkylamino groups are preferably lower alkoxy-substituted or mono- or di-lower alkylamino-substituted lower alkylamino group with 1–4, especially 1 or 2, carbon atoms in the alkyl part and 2–4, especially 2, carbon atoms in the alkylene part. Unsubstituted lower alkylamino can be straight-chain or branched and contains, for example, 1–7, especially 1–4, carbon atoms. Hydroxylamino, hydrazino, dimethylaminoethylamino, diethylaminoethylamino, ethoxyethylamino, butylamino, isopropylamino, propylamino, ethylamino and methylamino may be mentioned as examples of secondary amino groups.

Tertiary amino groups are, for example, amino groups substituted by two identical or different lower alkyl radicals with 1–7, especially with 1–4, carbon atoms, or amino groups substituted by straight-chain or branched lower alkylene which is optionally interrupted by a hetero-atom, such as sulphur, nitrogen or oxygen, and together with the amino nitrogen atom forms a 4–7-membered, especially 5-membered or 6-membered, ring. Examples of tertiary amino groups which may be mentioned are optionally C-lower alkylated, thiomorpholino, piperazino, piperidino, pyrrolidino, morpholino and N'-lower alkylpiperazino, such as N'-methylpiperazino or N'-ethylpiperazino, radicals, as well as dimethylamino, diethylamino, ethylmethylamino and dipropylamino.

The new compounds possess valuable pharmacological properties, above all an antipyretic and an anti-inflammatory action. Thus, for example, in the yeast-induced fever test they show, when orally administered in a dose of 3–30 mg/kg to rats, a distinct antipyretic action and, in the kaolin oedema test, when orally administered in a dose of 3–100 mg/kg, a distinct anti-inflammatory action. The compounds are therefore useful as antiphlogistics, as anti-rheumatic agents, as antipyretics and as mild analgesics.

The invention relates primarily to:

Compounds of the general formula I, wherein one of the two radicals $R_1$ and $R_2$ denotes a radical of the formula R—CO—, wherein R represents a benzoyl, pyridoyl or thenoyl radical which is optionally substituted by lower alkyl, lower alkoxy, halogen and/or trifluoromethyl, and the other denotes hydrogen or hydroxyl optionally esterified by a lower alkanecarboxylic acid or etherified by a lower alkanol, in each case with up to 7 carbon atoms, $R_3$ denotes hydrogen or lower alkyl or α-hydroxy-lower alkyl each with up to 4 carbon atoms, $R_4$ denotes a carboxyl group which is optionally esterified by a lower alkanol, which is substituted by an aryl radical which is optionally substituted by lower alkoxy, lower alkyl, halogen and/or trifluoromethyl, by a heteroaryl radical which is optionally substituted by lower alkyl or lower alkoxy, by lower alkoxy or by hydroxyl, or an amidised carboxyl group which contains, as the amino group, a di-lower alkylamino-lower alkylamino group, hydroxylamino, hydrazino, a mono- or di-lower alkylamino group or an optionally C-lower alkylated thiomorpholino, piperidino, pyrrolidino or N'-lower alkylpiperazino group, and $n$ denotes 0 or 1 and $m$ denotes 1 or 2.

The invention relates, in particular, to:

Compounds of the general formula I, wherein one of the two radicals $R_1$ and $R_2$ denotes a radical of the formula R—CO—, wherein R represents a benzoyl, pyridoyl or thenoyl radical which is optionally substituted by lower alkyl, lower alkoxy, halogen and/or trifluoromethyl, and the other denotes hydrogen, or hydroxyl which is optionally esterified by a lower alkanecarboxylic acid with 2 to 4 carbon atoms or etherified by a lower alkanol with 1 to 4 carbon atoms, $R_3$ denotes hydrogen or lower alkyl with up to 4 carbon atoms, $R_4$ denotes a carboxyl group which is optionally esterified by a lower alkanol, which can also be substituted by a phenyl or pyridyl radical which is optionally substituted by methyl, methoxy, chlorine and/or trifluoromethyl, by lower alkoxy or by hydroxyl, or an amidised carboxyl group which contains, as the amino group, hydroxylamino, hydrazino or an optionally N-mono-lower alkylated or N,N-dilower alkylated amino group, $n$ is 0 or 1 and $m$ is 1 or 2.

The invention relates, above all, to:

Compounds of the general formula I, wherein one of the radicals $R_1$ and $R_2$ denotes benzoyl, thenoyl or pyridoyl optionally substituted by methyl, methoxy, chlorine and/or trifluoromethyl and the other denotes hydrogen, acetoxy or hydroxyl, $R_3$ denotes hydrogen, $R_4$ denotes carboxyl optionally esterified by a lower alkoxyethanol, such as methoxyethanol or ethoxyethanol, a phenyl-lower alkanol, such as phenethyl alcohol or benzyl alcohol, a pyridylmethanol, a hydroxy-lower alkanol, such as ethylene glycol, propylene glycol or glycerol, or a lower alkanol with up to 4 carbon atoms, or denotes carbamyl, $n$ is 0 or 1 and $m$ is 1.

The invention relates especially to:

Compounds of the general formula I, wherein one of the radicals $R_1$ and $R_2$ denotes benzoyl optionally monosubstituted by lower alkyl or lower alkoxy with up to 4 carbon atoms, such as methoxy or methyl, trifluoromethyl or halogen, such as chlorine, and the other denotes hydroxyl, $R_3$ denotes hydrogen, $R_4$ denotes carboxyl optionally esterified by a lower alkanol with 1–4 carbon atoms, $n$ is 0 and $m$ is 1.

The invention relates specifically to:

The compounds of the general formula I named in the examples.

The new compounds can be manufactured according to methods which are in themselves known.

Thus, for example, a possible procedure is to introduce the acyl radical $R_2$ or $R_1$ of a carboxylic acid of aromatic character into a compound of the general formula II

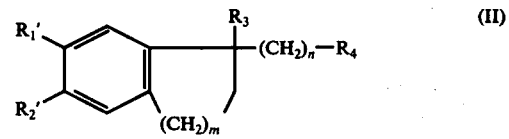

wherein one of the radicals $R_1'$ and $R_2'$ represents hydrogen and the other denotes hydrogen or optionally esterified or etherified hydroxyl $R_1$ or $R_2$ or an acyloxy radical $R_2O$ or $R_1O$ derived from a carboxylic acid of aromatic character, and $R_1$, $R_2$, $R_3$, $R_4$, $n$ and $m$ have the indicated meanings.

The introduction of the acyl radical $R_2$ or $R_1$ can be carried out in a manner which is in itself known, for example by C-acylation.

The C-acylation can be carried out in the customary manner, in particular in the manner known for analogous reactions from the literature, starting from compounds of the formula II, wherein one of the radicals $R_1'$ and $R_2'$ represents hydrogen and the other represents hydrogen or optionally esterified or etherified hydroxyl $R_1$ or $R_2$, by reaction with preferably functionally modified carboxylic acid of aromatic character, of the formula $R_2$—OH or $R_1$—OH, or starting from a compound of the formula II, wherein one of the radicals $R_1'$ and $R_2'$ is hydrogen and the other is an acyloxy radical $R_2O$— or $R_1O$— derived from a carboxylic acid of aromatic character, by a rearrangement leading to hydroxy compounds ($R_1$ or $R_2$ = OH).

Optionally functionally suitably modified carboxylic acids $R_2$—OH and $R_1$—OH are, for example, these acids themselves, or the nitriles, but preferably anhydrides of these acids, such as the anhydrides of these acids or mixed anhydrides of these acids with other organic acids, for example with lower alkanecarboxylic acids or organic sulphonic acids, or, above all, with inorganic acids, for example with hydrogen halide acids, for example with hydrochloric acid or hydrobromic acid.

The abovementioned reaction of an optionally functionally suitably modified carboxylic acid with a compound of the formula II, and its rearrangement to compounds of the formula I, can be carried out in the usual manner, for example in the presence of an acid catalyst, such as a Lewis acid, for example a suitable metal halide, such as aluminium chloride or aluminium bromide, boron trifluoride, zinc chloride or antimony trichloride, or a strong protonic acid, such as sulphuric acid or polyphosphoric acid, advantageously in an inert solvent, such as a halogenohydrocarbon, for example in chlorobenzene, carbon tetrachloride, or dichloromethane or tetrachloroethane, in carbon disulphide or in nitrobenzene, if necessary with application of energy, for example thermally at a reaction temperature between 0° and 150°, preferably 0°-100°, and/or photochemically, for example in the case of the rearrangement of compounds of the formula II, wherein one of the radicals $R_1'$ and $R_2'$ is hydrogen and the other is an acyloxy group $R_2O—$ or $R_1O—$.

The new compounds can furthermore be obtained by oxidising the radical Y to the acyloxy radical $R_2$ or $R_1$ of a carboxylic acid or aromatic character, in a compound of the general formula III

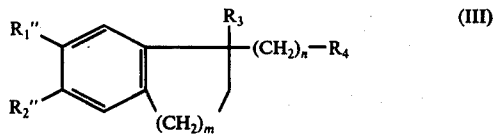

wherein one of the radicals $R_1''$ and $R_2''$ is hydrogen or optionally esterified or etherified hydroxyl and the other denotes an aryl- or heteroaryl-hydroxymethyl radical corresponding to an acyl radical $R_2$ or $R_1$ and $R_1$, $R_2$, $R_3$, $R_4$, $n$ and $m$ have the indicated meanings.

An arylhydroxymethyl or heteroarylhydroxymethyl radical is, for example, a group of the formula R—CH(OH)—, wherein R has the indicated meaning.

The oxidation can be carried out in the usual manner, for example by means of a customary oxidising agent, for example with an inorganic oxidising agent, such as with a complex of dimethylsulphoxide and chlorine in the presence of a tertiary amine, for example of triethylamine, or with sodium periodate, preferably in the presence of ruthenium oxide and of water, with a copper-(II) salt, for example copper-(II) acetate or copper-(II) sulphate, with bismuth oxide, with manganese dioxide or above all with chromic acid or chromium trioxide, advantageously in a solvent which is inert towards the oxidising agent used, for example in a lower alkanecarboxylic acid, such as acetic acid, or in pyridine, quinoline or similar heterocyclic bases, or with organic oxidising agents, for example with N-chlorosuccinimide in the presence of a dialkyl sulphide, such as of dimethyl sulphide, or with hypohalites, for example with tert.-butyl hypochlorite, or halogenated quinones, for example with chloranil, or in particular with aldehydes or above all ketones, for example with lower alkanones, cycloalkanones or quinones, such as acetone, cyclohexanone or benzoquinone, in the presence of suitable catalysts, such as metal salts, especially aluminum salts, of branched lower alkanols or phenols, for example with aluminium isopropylate, aluminium tert.-butylate or aluminium phenolate, here again preferably in a solvent, especially an excess of the ketone used and/or of the alcohol corresponding to the metal alcoholate used. However, in carrying out the oxidation, care must be taken that other oxidisable groups should not be attacked.

The new compounds can furthermore be prepared by converting Z into a group $R_4$ in a compound of the general formula IV

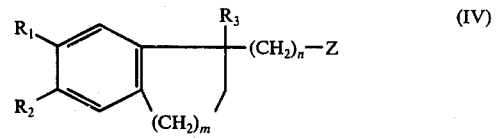

wherein $R_1$, $R_2$, $R_3$, $R_4$, $n$ and $m$ have the indicated meanings and Z denotes a functionally modified carboxyl group which differs from esterified or amidised carboxyl groups $R_4$.

Functionally modified carboxyl groups Z which differ from esterified or amidised carboxyl groups are, for example, groups of the formula $—CZ_1Z_2Z_3$ wherein $Z_1$, $Z_2$ and $Z_3$ conjointly represent the nitrilo group or $Z_1$ and $Z_2$ conjointly represent the oxo or imino group and $Z_3$ denotes a halogen atom or, if $Z_1 + Z_2$ denotes imino, an etherified hydroxyl group. The group of the formula $—C≡C=O$ should further be mentioned as a group which can be converted into an optionally esterified or amidised carboxymethyl group.

Etherified hydroxyl groups $Z_3$ are, for example, hydroxyl groups etherified with lower alkanols, such as methanol or ethanol, or with lower alkanediols, such as ethylene glycol or a propylene glycol. Halogen atoms $Z_3$ are; for example, chlorine or bromine.

The conversion of a functionally modified carboxyl group Z′ which differs from esterified or amidised carboxyl groups $R_4$ into groups of the formula $R_4$, and of the group of the formula $—C≡C=O$ into groups of the formula $—CH_2R_4$ can be carried out in the usual manner, by solvolysis, that is to say hydrolysis (reaction with water), alcoholysis (reaction with an alcohol) or aminolysis (reaction with ammonia or an amine having at least one hydrogen atom).

By hydrolysis it is possible to convert, for example, the group of the formula $—C≡C=O$ into the carboxymethyl group, or a functionally modified carboxyl group Z into the free carboxyl group, or a nitrile group Z of the formula $—CZ_1Z_2Z_3$, wherein $Z_1$, $Z_2$ and $Z_3$ conjointly represent the nitrilo group, into the carbamoyl group $R_4$, or an iminoether group Z′, of the formula $—CZ_1Z_2Z_3$, wherein $Z_1$ and $Z_2$ conjointly represent the imino group and $Z_3$ denotes an etherified hydroxyl group, into esterified carboxyl groups $R_4$. The hydrolysis can be carried out in the usual manner, preferably in the presence of a catalyst, for example of a strong base, such as an alkali metal hydroxide or carbonate or alkaline earth metal hydroxide or carbonate, for example sodium hydroxide or carbonate or potassium hydroxide or carbonate, or of a strond acid, such as a mineral acid, for example hydrochloric acid, sulphuric acid or phosphoric acid, or of a carboxylic acid, for example acetic acid, if necessary with addition of nitrous acid when hydrolysing a nitrile group Z′ to the free carboxyl group.

By alcoholysis it is possible to convert, for example, a cyano group, an acid, halide grouping Z of the formula $-CZ_1Z_2Z_3$, wherein $Z_1$, $Z_2$ and $Z_3$ denote the nitrilo group or $Z_1$ and $Z_2$ conjointly represent the oxo group and $Z_3$ denotes halogen atom group, into an esterified carboxyl group $R_4$, or to convert the ketene group of the formula $-C=C=O$ into an esterified carboxymethyl group $-CH_2-R_4$.

The alcoholysis can be carried out in the usual manner, for example in the presence of a basic agent, such as an alkali metal alcoholate, for example sodium alcoholate or potassium alcoholate, or of an inorganic base, for example sodium hydroxide or carbonate or potassium hydroxide or carbonate, or calcium carbonate, or an organic nitrogen base, for example triethylamine or pyridine, or starting from nitriles, in the presence of hydrohalides of nitrogen bases, for example of ammonium chloride or pyridinium bromide, and in the presence of an approximately equimolecular amount of water, if necessary at an elevated temperature.

By aminolysis it is possible to convert, for example, an acid halide grouping Z of the formula $-CZ_1Z_2Z_3$, $Z_1$ and $Z_2$ conjointly representing the oxo group and $Z_3$ denoting a halogen atom into an amidised carboxyl group $R_4$, or to convert the ketone group $-C=C=O$ into an amidised carboxymethyl group $-CH_2-R_4$.

The aminolysis can be carried out in a manner which is in itself known, preferably in the presence of a basic condensation agent, such as an inorganic base, for example sodium hydroxide or carbonate or potassium hydroxide or carbonate, or calcium carbonate, or a nitrogen base, such as an excess of the ammonia or amine used for the aminolysis, or a tertiary organic nitrogen base, for example triethylamine or pyridine, if necessary at elevated temperature.

In resulting compounds, substituents can be introduced, modified or split off, within the scope of the definition of the end product.

Thus, for example, free, esterified and amidised carboxyl groups $R_4$ can be converted into one another.

Thus, a free carboxyl group can be esterified, to give an esterified carboxyl group $R_4$, by reaction with an alcohol or a reactive derivate of an alcohol, such as a carboxylic acid ester or carbonic acid ester, for example a lower alkanecarboxylic acid ester of the carbonate, or a mineral acid ester or sulphonic acid ester, for example the hydrochloric acid ester, hydrobromic acid ester, sulphuric acid ester, benzenesulphonic acid ester, toluenesulphonic acid ester or methanesulphonic acid ester, of an alcohol or an olefine derived therefrom.

The reaction with an alcohol can be carried out in the usual manner, advantageously in the presence of an acid catalyst such as a protonic acid, for example hydrochloric acid or hydrobromic acid, sulphuric acid, phosphoric acid, boric acid, benzenesulphonic acid and/or toluenesulphonic acid, or of a Lewis acid, for example boron trifluoride ethereate, in an inert solvent, especially in an excess of the alcohol employed, and, if necessary, in the presence of a water-binding agent and/or whilst removing the water of reaction by distillation, for example by azeotropic distillation, and/or at elevated temperatures.

The reaction with a reactive derivative of an alcohol can be carried out in the usual manner, starting from a carboxylic acid ester or carbonic acid ester, for example in the presence of an acid catalyst, such as one of those mentioned, in an inert solvent, such as an ether, for example diethyl ether or tetrahydrofurane, a hydrocarbon, for example benzene or toluene, or a halogenohydrocarbon, for example trichloroethane or tetrachloroethane, chloroform, carbon tetrachloride or methylene chloride, or an excess of the alcohol derivative employed or of the corresponding alcohol, if necessary whilst distilling off the water of reaction, eg. azeotropically. If the starting material is a mineral acid ester or sulphonic acid ester, the acid to be esterified is advantageously employed in the form of a salt, for example the sodium salt or potassium salt, and the reaction is carried out, if necessary, in the presence of a basic condensation agent, such as an inorganic base, for example sodium carbonate, potassium carbonate or calcium hydroxide or carbonate, or of a tertiary organic nitrogen base, for example triethylamine or pyridine, in an inert solvent, such as one of the abovementioned tertiary nitrogen bases or a polar solvent, for example phosphoric acid tris(dimethylamide), and/or at an elevated temperature.

The reaction with an olefine can be carried out, for example, in the presence of an acid catalyst, e.g. a Lewis acid, e.g. boron trifluoride, a sulphonic acid, e.g. benzenesulphonic acid, toluenesulphonic acid or methanesulphonic acid, or, above all, a basic catalyst, for example a strong base, such as an alkali metal hydroxide or carbonate or alkaline earth metal hydroxide or carbonate, for example sodium hydroxide or carbonate or potassium hydroxide or carbonate, advantageously in an inert solvent, such as an ether, for example diethyl ether or tetrahydrofurane, a hydrocarbon, for example an alkane, benzene or toluene, or a halogenohydrocarbon, for example tetrachloroethane or trichloroethane, chloroform, methylene chloride or carbon tetrachloride.

A free carboxyl group $R_4$ can furthermore be converted into an amidised carboxyl group $R_4$ by reaction with ammonia or with an amine possessing at least one hydrogen atom, in the usual manner, for example with dehydration of the ammonium salt formed as an intermediate, for example by azeotropic distillation with benzene or toluene, or by dry heating.

The conversions of free carboxyl groups to esterified or amidised carboxyl groups $R_4$, described above, can however also be carried out by first converting the resulting acid of the formula I in the usual manner, into a reactive derivative, for example into an acid halide by means of a halide of phosphorus or sulphur, such as phosphorus trichloride or tribromide, phosphorus pentachloride or thionyl chloride, or into a reactive ester, that is to say an ester containing electron-attracting structures, such as the ester with phenol, thiophenol, p-nitrophenol or cyanomethyl alcohol, by reaction with a corresponding alcohol, or into a reactive amide, for example the amide derived from imidazole or 3,5-dimethylpyrazole, by reaction with a corresponding amine, and then reacting the resulting reactive derivative in the usual manner, for example as described above for the alcoholysis or aminolysis of groups Z' or described below for the trans-esterification, transamidation or interconversion of esterified and amidised carboxyl groups $R_4$, with an alcohol, ammonia or an amine possessing at least one hydrogen atom.

An esterified carboxyl group $R_4$ can be converted into the free carboxyl group $R_4$ in the usual manner, for example by hydrolysis in the presence of a catalyst, for example a strong base, such as an alkali metal hydroxide or carbonate or alkaline earth metal hydroxide or carbonate, for example sodium hydroxide or carbonate or potassium hydroxide or carbonate, or a strong acid, such as a mineral acid, for example hydrochloric acid, sulphuric acid or phosphoric acid, or a carboxylic acid, for example acetic acid, or can be converted to an amidised carboxyl group $R_4$, for example by reaction with ammonia or an amine possessing at least one hydrogen atom.

An esterified carboxyl group $R_4$ can furthermore be trans-esterified to another esterified carboxyl group $R_4$ in the usual manner, for example by reaction with a metal salt, such as the sodium salt or potassium salt, of an alcohol, or by reaction with the alcohol itself in the presence of a catalyst, for example a strong base, such as an alkali metal hydroxide or carbonate or alkaline earth metal hydroxide or carbonate, for example sodium hydroxide or carbonate or potassium hydroxide or carbonate, or a strong acid, such as a mineral acid, for example hydrochloric acid, sulphuric acid or phosphoric acid, or a carboxylic acid, for example acetic acid, benzenesulphonic acid or toluenesulphonic acid, or a Lewis acid, for example boron trifluoride etherate.

An amidised carboxyl group $R_4$ can be converted into the free carboxyl group $R_4$ in the usual manner, for example by hydrolysis in the presence of a catalyst, for example a strong base, such as an alkali metal hydroxide or carbonate or alkaline earth metal hydroxide or carbonate, for example sodium hydroxide or carbonate or potassium hydroxide or carbonate, or a strong acid, such as a mineral acid, for example hydrochloric acid, sulphuric acid or phosphoric acid.

In resulting compounds it is furthermore possible to convert free hydroxyl groups and esterified or etherified hydroxyl groups $R_1$ or $R_2$ into one another.

Thus, for example, a free hydroxyl group can be esterified by reaction with a preferably functionally modified acid, for example a lower alkanecarboxylic acid, for example to give a lower alkanoyloxy group $R_1$ or $R_2$, or can be etherified by reaction with an etherifying agent, for example with a lower alkylating agent, for example to give a lower alkoxy group $R_1$ or $R_2$.

A functionally modified acid, for example lower alkanecarboxylic acid is, for example, an anhydride, such as the anhydride, for example a lower alkanecarboxylic acid anhydride, an anhydride with a halogen halide acid, such as hydrochloric acid or hydrobromic acid, for example a lower alkanecarboxylic acid chloride or bromide, or the inner anhydride, for example a lower alkyl-ketene, a reactive ester, that is to say an ester with electron-attracting structures, for example a lower alkanecarboxylic acid phenyl ester, p-nitrophenyl ester or cyanomethyl ester, or a reactive amide, for example a N-lower alkanoylimidazole or N-lower alkanoyl-3,5-dimethylpyrazole.

Examples of etherifying agents are reactive esterified alcohols, such as alcohols esterified with a mineral acid, for example with hydriodic acid, hydrochloric acid or hydrobromic acid, fluorosulphonic acid or sulphuric acid, or organic sulphonic acids, for example p-toluenesulphonic acid, p-bromobenzenesulphonic acid, benzenesulphonic acid, methanesulphonic acid, ethanesulphonic acid or ethenesulphonic acid, as well as diazoalkanes. Examples of lower alkylating agents to be mentioned are therefore lower alkyl chlorides, iodides and bromides, for example methyl iodide, di-lower alkyl sulphates, for example dimethyl sulphate or diethyl sulphate or methyl fluorosulphonate, lower alkyl sulphonates, such as lower alkyl, for example methyl, p-toluenesulphonates, p-bromobenzenesulphonates, methanesulphonates or ethanesulphonates, as well as diazoalkanes, for example diazomethane.

The reactions with preferably functionally modified acids or with etherifying agents, for example those singled out above, can be carried out in the usual manner, in the case of the reaction with diazoalkanes in an inert solvent, such as an ether, for example diethyl ether, or in the case of the reaction of reactive esterified alcohols, for example, in the presence of a basic condensation agent, such as an inorganic base, such an an alkali metal hydroxide or carbonate, or alkaline earth metal hydroxide or carbonate, for example sodium hydroxide or carbonate or potassium hydroxide or carbonate, or calcium hydroxide or carbonate, or a tertiary or quaternary nitrogen base, for example pyridine, α-picoline, quinoline, triethylamine, tetraethylammonium hydroxide or benzyltriethylammonium hydroxide, and/or in the presence of a solvent customary for the particular reaction, which solvent can also consist of an excess of the functional acid derivative used for the esterification, for example a lower alkanoic acid anhydride or lower alkanoic acid chloride, or of the lower alkyl halide or lower alkyl sulphate used, for example, for the esterification, and/or of a tertiary nitrogen base used as the basic condensation agent, for example triethylamine or pyridine, if necessary at elevated temperatures.

Particular methods of carrying out the reaction which are to be recommended are methylation by means of methyl iodide in amyl alcohol/potassium carbonate at the boil, and acylation by means of a lower alkanoic acid anhydride at 50°-150° or by means of a lower alkanoyl chloride in pyridine or pyridine/triethylamine at temperatures between −20° and +100° C.

Conversely, it is also possible to convert etherified or, above all, esterified hydroxyl groups $R_1$ or $R_2$ into the free hydroxyl group, for example by hydrolysis. These conversions can be carried out in the usual manner, in the case of the hydrolysis, for example, in the manner described initially for the hydrolysis of functionally modified carboxyl groups $Z'$ to the free carboxyl group. The conversion of an etherified hydroxyl group into a free hydroxyl group can however also be carried out conjointly with the acylation, described above, of starting materials of the formula II which contain an etherified hydroxyl group $R_1'$ or $R_2'$. Under drastic reaction conditions, for example when using aluminum chloride as the catalyst, this gives, alongside or in place of end products of the formula I, wherein $R_1$ and $R_2$ denotes an etherified hydroxyl group, also the corresponding compounds in which a free hydroxyl group $R_1$ or $R_2$ is present.

The reactions mentioned can optionally be carried out simultaneously or successively, and in any desired sequence.

The reactions mentioned are carried out in the usual manner, in the presence or absence of diluents, condensation agents and/or catalysts, at lowered, ordinary or elevated temperatures, if appropriate in a closed vessel.

Depending on the process conditions and starting materials, end products which form salts may be obtained in the free form or in the form of their salts which can be converted in the usual manner into one another or into other salts. Thus acid end products, such as carboxylic acids or hydroxamic acids are obtained in the free form or in the form of their salts with bases. Free acid compounds obtained can be converted into the salts with a base, for example salts with organic amines, or metal salts, in the usual manner, for example by reaction with corresponding basic agents. Metal salts can be, above all, alkali metal salts or alkaline earth metal salts, such as sodium salts, potassium salts, magnesium salts or calcium salts. Free acids can be liberated from the salts in the usual manner, for example by reaction with acid agents. Equally, basic compounds are obtained in the free form or in the form of their salts with acids. Resulting salts with acids can be converted into the free compounds in a manner which is in itself known, for example by means of alkalis or ion exchangers. Salts can be obtained from the free compounds by reaction with organic or inorganic acids, especially those suitable for forming therapeutically usable salts. As examples of such acids there may be mentioned: hydrogen halide acids, sulphuric acids, phosphoric acids, nitric acid, perchloric cid, aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicyclic acid or p-aminosalicyclic acid, embonic acid, methanesulphonic acid, ethanesulphonic acid, hydroxyethanesulphonic acid and ethylenesulphonic acid; halogenobenzenesulphonic acids, toluenesulphonic acid, naphthalenesulphonic acid or sulphanilic acid; methionine, tryptophan, lysine or arginine.

These and other salts can also be used to purify the new compounds, for example by converting the free compounds to their salts, isolating these and reconverting the salts to the free compounds. Because of the close relationships between the new compounds in the free form and in the form of their salts, the free compounds are, in the preceding and following text, where appropriate also to be understood to include the corresponding salts, in respect of general sense and intended use.

The invention also relates to those embodiments of the process according to which a compound obtainable as an intermediate product at any stage of the process is used as the starting material and the missing steps are carried out, or a starting material is used in the form of a salt and/or racemate or antipode or, in particular, is formed under the reaction conditions.

Thus it is possible, for example, in the oxidation of compounds of the formula III to start from a corresponding starting material wherein Y is the arylmethyl or heteroarylmethyl radical, for example of the formula —CH$_2$—R, derived from the acyl radical of a carboxylic acid. In this case, the corresponding hydroxymethyl radical, for example of the formula —CH(OH)—R, is formed as an intermediate stage and is then oxidised further in accordance with the invention.

Furthermore it is possible, in the solvolysis of compounds of the formula IV, wherein Z represents a —C=C=O group, to start from the corresponding diazoketone, wherein Z represents a —CO—CH—N$_2$+group, and to react this compound with water, an alcohol, ammonia or an amine possessing at least one hydrogen atom, if required in the presence of a catalyst, for example of silver or a silver compound, such as silver oxide, and/or at an elevated temperature. In this reaction, the corresponding ketene, wherein Z is the —C=C=O group, is produced as an intermediate, and this is then solvolysed, in accordance with the invention, to an optionally esterified or amidised carboxymethyl group —CH$_2$R$_4$.

The oxidation is carried out in the usual manner with an oxidising agent in an alkaline, neutral or acid solution, such as with silver oxide and alkali, for example sodium hydroxide solution, with aqueous potassium permanganate solution, or with an acid chromate solution, for example a chromate solution containing sulphuric acid, for example at room temperature or by warming.

The new compounds can, depending on the choice of the starting materials and procedures, be in the form of one or more of the particular stereoisomers which are possible, for example in the form of positional isomers with respect to the position of R$_1$ and R$_2$, or of mixtures thereof, and, depending on the number of asymmetrical carbon atoms, in the form of pure optical isomers, for example optical antipodes, or of isomer mixtures, such as racemates, diastereomer mixtures or racemate mixtures.

Resulting stereoisomer mixtures, such as diastereomer mixtures or mixtures of positional isomers and/or racemate mixtues, can be separated into the pure isomers, such as positional isomers or diastereomers or racemates, on the basis of the physico-chemical differences of the constituents, in a known manner, for example by chromatography and/or fractional crystallisation.

Resulting racemates can be resolved into the optical antipodes in accordance with known methods, for example by recrystallisation from an optically active solvent, by means of micro-organisms, or by reaction of an end product with an optically active acid or base which forms salts with the racemate and separation of the salts obtained in this manner, for example on the basis of their different solubilities, into the diastereomers, from which the antipodes can be liberated by treatment with suitable agents. Particularly customary optically active acids are, for example, the D- and L-forms of tartaric acid, di-o-toluyltartaric acid, malic acid, mandelic acid, camphorsulphonic acid or quinic acid. Advantageously, the more active of the two antipodes is isolated.

Examples of preferred optically active bases are brucine, strychnine, morphine, menthylamine or α-phenylethylamine or their quaternary ammonium bases. Advantageously, the more active or less toxic of the two antipodes is isolated.

Preferably, those starting materials are used to carry out the reactions according to the invention which give the groups of end products particularly mentioned initially, and especially the end products which have been specifically described or single out.

The starting materials are known or can, if they are new, be prepared according to methods which are in themselves known. Thus, starting materials of the general formula II can be obtained, for example, by reducing the oxo group in a compound of the formula V

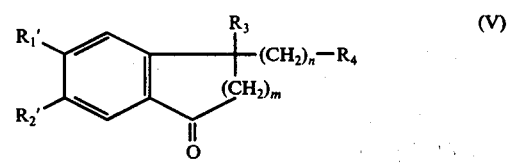

wherein R$_1$', R$_2$', R$_3$, R$_4$, n and m have the indicated meanings. The reduction of the oxo group can be effected, for example, in accordance with the Wolff-Kishner method by conversion to a hydrazone or semicarbazone and reaction with an alkali metal alcoholate, for examle sodium ethylate, preferably under pressure and/or at elevated temperatures, or in accordance with the Huang-Minlon method by heating with hydrazine and an alkali metal hydroxide in a high-boiling solvent, such as diethylene glycol or diethylene glycol monomethyl ether, or by treatment with nascent or catalytically activated hydrogen, for example by reaction with a metal, such as zinc or iron, and an acid, for example hydrochloric acid or acetic acid, or by treatment with elementary hydrogen in the presence of a hydrogenation catalyst such as palladium/charcoal, if necessary under elevated pressure and/or at elevated temperatures.

Compounds of the formula V, wherein $n = 0$, $m = 1$ and $R_3$ is hydrogen is alkyl, can be prepared by condensing a 3-$R_1'$-4-$R_2'$-benzaldehyde or a corresponding alkyl phenyl ketone with a malonic acid lower alkyl ester, adding hydrocyanic acid to the resulting benzylidenemalonic acid ester in the manner of a Michael addition, saponifying and decarboxylating the resulting α-cyano-α-$R_3$-3-$R_1'$-4-$R_2'$-benzylmalonic acid ester to give β-carboxy-β-$R_3$-β-(3-$R_1'$-4-$R_2'$-benzyl)propionic acid and cyclising the latter by means of sulphuric acid or polyphosphoric acid or after conversion into the chloride, by means of aluminum chloride.

Compounds of the formula V, wherein $n = 0$, $m = 2$ and $R_3$ is hydrogen or alkyl can be obtained, for example, by reacting a α-$R_3$-α-(3-$R_1'$-4-$R_2'$phenyl)-acetic acid alkyl ester or α-$R_3$-α-(3-$R_1'$-4-$R_2'$phenyl)-acetonitrile with an acrylonitrile or acrylic acid alkyl ester, saponifying the resulting γ-carboxy-β-(3-$R_1'$-4-$R_2'$-phenyl)-butyric acid nitrile or -butyric cid alkyl ester to the corresponding γ-carboxy-β-(3-$R_1'$-4-$R_2'$-phenyl)-butyric acid and cyclising the latter, for example as described above.

Compounds of the formula II, Wherein $n = 1$, can furthermore be prepared, starting from the corresponding 5-$R_2'$-6-$R_1'$-1-indanone or 6-$R_2'$-7-$R_1'$-α-tetralone, in accordance with the Reformatzky reaction, by reacting them with an α-metal-acetic acid alkyl ester, for example α-zinc-acetic acid alkyl ester, to give the corresponding indene- or 3,4-dihydronaphthalene-acetic acid ester, hydrogenating the ester and, if required, saponifying and/or otherwise functionally modifying the product.

Compounds of the formula II, wherein $n = 0$, can furthermore be prepared analogously by reaction of the above 1-indanones or α-tetralones with methoxymethylene-triphenylphosphorane, hydrolysis to the aldehyde and oxidation thereof.

Starting materials of the formula III can be prepared, for example, from compounds of the formula II indicated above, by introducing the formyl group instead of hydrogen $R_1'$ or $R_2'$, for example in accordance with the Vilsmeyer reaction, and/or reaction of the aldehyde thus obtainable with a metal compound, for example the lithium compound, of a compound of the formula R—H.

Iminoethers and iminohalides of the formula IV, wherein Z denotes a —$CZ_1Z_2Z_3$ group, $Z_3$ denotes a halogen atom or an etherified hydroxyl group and $Z_1 + Z_2$ denotes the imino group, can be prepared, for example, by cyclisation of a β-cyano-β-(3-$R_1$-4-$R_2$-phenyl)-β-$R_3$-acetic acid or γ-cyano-γ-(3-$R_1$-4-$R_2$-phenyl)-γ-$R_3$-propionic acid or of a functional carboxy derivative thereof, which can be prepared, for example, by reaction of an α-$R_3$-3-$R_1$-4-$R_2$-benzylidenemalonic ester with an alkali metal cyanide, decarboxylation and hydrolysis, or reaction of an α-$R_3$-3-$R_1$-4-$R_2$-acetonitrile with acrylic esters and hydrolysis and, if desired, functional modification of the resulting acid, and reaction of the resulting nitrile with an acid to give the iminoester, and, if desired, with an alcohol to give the iminoether.

In the processes for the preparation of the starting materials, explained above, $R_1$, $R_1'$, $R_2$, $R_2'$, $R_3$, $R_4$, $n$ and $m$ unless stated otherwise, each have the initially mentioned meanings, especially the meanings initially singled out.

The pharmacologically utilisable compounds of the present invention can be used, for example, to produce pharmaceutical preparations, for example for the treatment of fever, for the treatment of illnesses of the rheumatic type, or for the treatment of non-infectious inflammation conditions and/or pains of medium severity, which preparations contain an effective amount of the active substance together with, or mixed with, inorganic or organic, solid or liquid, pharmaceutically usable excipients which are suitable for enteral, for example oral or parenteral administration or topical application. Preferably, tablets or gelatine capsules are used, which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium silicate, starches, such as maize starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, enzymes for the binders and/or effervescent mixtures, or absorbents, dyestuffs, flavouring substances and sweeteners. Injectable preparations are preferably isotonic aqueous solutions or suspensions, suppositories or ointments, above all fat emulsions or fat suspensions. The pharmacological preparations can be sterilised and/or contain auxiliaries, for example preservatives, stabilisers, wetting agents and/or emulsifiers, solubilising agents, salts for regulating the osmotic pressure and/or buffers. The present pharamaceutical preparations which can, if desired, contain further pharmacologically valuable materials, are prepared in a manner which is in itself known, for example by means of conventional mixing, granulating or dragee-making processes, and contain from about 0.1 to about 75%, in particular from about 1 to about 50%, of the active compound. The recommended daily dose for a warm-blooded animal weighing about 75 kg is 25–250 mg.

The invention is described in more detail in the examples which follow.

EXAMPLE 1

40 g of finely powdered aluminum chloride are added in portions to a stirred solution of 20.6 g of 6-methoxy-indane-1-carboxylic acid methyl ester and 15.5 g of benzoyl chloride in 200 ml of absolute methylene chloride at 20° C, in an anhydrous atmosphere, stirring is continued overnight at room temperature and the reaction solution is then poured onto 500 g of ice and extracted with 3 times 100 ml of methylene chloride. The organic phases are washed successively with 500 ml of saturated sodium bicarbonate solution, 500 ml of 2 N hydrochloric acid and 500 ml of water, dried over anhydrous sodium sulphate and evaporated in vacuo. The evaporation residue, when crystallized from ether-petroleum ether after treatment with active charcoal, gives 5-benzoyl-6-hydroxy-indane-1-carboxylic acid methyl ester of melting point 89°–91° C.

EXAMPLE 2

A solution of 8.2 g of 5-benzoyl-6-hydroxy-indane-1-carboxylic acid methyl ester in 150 ml of methanol is mixed with 20 ml of 2 N sodium hydroxide solution and the mixture is boiled for 3 hours under reflux. It is then evaporated to dryness in vacuo and the evaporation residue is partitioned between 100 ml of 2 N hydrochloric acid and 3 times 100 ml of methylene chloride. The organic phases are washed until neutral, dried over sodium sulphate, treated with active charcoal and evaporated in vacuo. The evaporation residue, when crystalized from ethanol-petroleum ether, gives 5-benzoyl-6-hydroxy-indane-1-carboxylic acid in the form of yellow platelets of melting point 185–7° C.

EXAMPLE 3

A solution of 12 g of 5-benzoyl-6-hydroxy-indane-1-carboxylic acid in 100 ml of n-butanol and 8 drops of concentrated sulphuric acid is boiled for 6 hours under reflux in an anhydrous atmosphere. It is then evaporated to a volume of approx. 20 ml in vacuo and the evaporation residue is partitioned between 3 times 100 ml of methylene chloride and 3 times 100 ml of water. The organic phases are dried over sodium sulphate and evaporated in vacuo. The evaporation residue, when crystallized from cold ether-petroluem ether, gives 5-benzoyl-6-hydroxy-indane-1-carboxylic acid n-butyl ester in the form of yellow platelets of melting point 43°–44° C.

EXAMPLE 4

Analogously to Example 3, 12 g of 5-benzoyl-6-hydroxyindane-1-carboxylic acid and ethanol containing sulphuric acid give 5-benzoyl-6-hydroxy-indane-1-carboxylic acid ethyl ester in the form of yellow platelets of melting point 83–4° C.

EXAMPLE 5

A solution of 20.6 g of 6-methoxy-indane-1-carboxylic acid methyl ester in a little methylene chloride is first slowly added dropwise, at 0° to 10° C, to a suspension of 66.8 g of finely powdered aluminum chloride in 100 ml of methylene chloride, which is being stirred under anhydrous conditions; 46.3 g of p-methylbenzoyl chloride are then added dropwise under such conditions that the reaction mixture boils gently under reflux. After completion of the addition, the mixture is heated to the boil for a further 3½ hours. It is then allowed to cool to room temperature, poured onto 500 g of ice and extracted with twice 500 ml of methylene chloride. The organic phases are washed until neutral, dried over sodium sulphate and evaporated in vacuo (finally in a high vacuum). The evaporation residue, when crystallized from cold ether-petroleum ether, gives 5-(p-toluoyl)-6-hydroxyindane-1-carboxylic acid methyl ester which after a further crystallisation from ethanol-petroluem ether, melts at 74°–76° C.

EXAMPLE 6

Analogously to the method described in Example 2, 8.5 g of 5-(p-toluoyl)-6-hydroxy-indane-1-carboxylic acid methyl ester give 5-(p-toluoyl)-6-hydroxy-indane-1-carboxylic acid in the form of yellow crystals of melting point 186–8° C (from ether).

EXAMPLE 7

Analogously to the process described in Example 5, 19 g of 6-methoxy-indane-1-carboxylic acid methyl ester and 48 g of p-chlorobenzoyl chloride give 5-(p-chlorobenzoyl)-6-hydroxy-indane-1-carboxylic acid methyl ester of melting point 96°–98° C (from ether-petroleum ether.

EXAMPLE 8

Analogously to the process described in Example 2, 10 g of 5-(p-chlorobenzoyl)-6-hydroxy-indane-1-carboxylic acid methyl ester give 5-(p-chlorobenzoyl)-6-hydroxy-indane-1-carboxylic acid in the form of dark yellow crystals of melting point 187–9° C (from ethanol-petroleum ether).

EXAMPLE 9

A solution of 10 g of 5-benzoyl-6-hydroxy-indane-1-carboxylic acid methyl ester in 100 ml of acetic anhydride is heated to the reflux temperature for 4 hours under anhydrous conditions. It is then evaporated to dryness in vacuo. The evaporation residue is mixed with 200 ml of toluene and evaporated in vacuo. Distillation of the evaporation residue in a high vacuum gives, in the fraction boiling at 195°–200° C/0.06 /mm Hg, 5-benzoyl-6-acetoxy-indane-1-carboxylic acid methyl ester in the form of a colourless oil.

EXAMPLE 10

Analogously to the description in Example 1, 15.5 g of 6-methoxy-indane-1-carboxylic acid methyl ester and 33 g of thiophene-2-carboxylic acid chloride give, after chromatographic purification of the crude product on 300 g of silica gel using methylene chloride as the eluting agent, 5-thenoyl-6-hydroxy-indane-1-carboxylic acid methyl ester of melting point 111°–113° C (from ether-petroleum ether).

EXAMPLE 11

Analogously to the description in Example 2, 4.0 g of 5-thenoyl-6-hydroxy-indane-1-carboxylic acid methyl ester and 20 ml of 2N sodium hydroxide solution in 50 ml of methanol give 5-thenoyl-6-hydroxy-indane-1-carboxylic acid of melting point 183°–184° C (from ethyl acetate/petroleum ether).

EXAMPLE 12

Analogously to the description in Example 1, 14.5 g of 6-methoxy-indane-1-carboxylic acid methyl ester and 36.8 g of o-chlorobenzoyl chloride give 5-(o-chlorobenzoyl)-6-hydroxy-indane-1-carboxylic acid methyl ester of melting point 78°–80° C (from ether-petroleum ether).

EXAMPLE 13

Analogously to the description in Example 2, 8.7 g of 5-(o-chlorobenzoyl)-6-hydroxy-indane-1-carboxylic acid methyl ester and 27 ml of 2 N sodium hydroxide solution in 100 ml of methanol give 5-(o-chlorobenzyl)-6-hydroxy-indane-1-carboxylic acid of melting point 188°–190° C (from ethyl acetate-petroleum ether).

EXAMPLE 14

A solution of 10.3 g of 6-methoxy-indane-1-carboxylic acid methyl ester in 200 ml of absolute methylene chloride is added slowly to 33 g of finely powdered aluminum chloride at −10° C, whilst excluding moisture. 21 g of benzoyl chloride are added dropwise over the course of 1 hour to the resulting suspension, whilst stirring at −10° to −5° C. After completion of the addition, the mixture is stirred for a further hour at −10° to −5° C. The reaction mixture is then poured onto 200 g of ice and extracted with 3 times 50 ml of methylene chloride. The organic phases are combined, washed with twice 200 ml of water, dried over sodium sulphate and evaporated in vacuo. The excess benzoyl chloride is distilled off under reduced pressure at 100° C. On triturating the distillation residue with ether-petroleum ether, 5-benzoyl-6-methoxy-indane-1-carboxylic acid methyl ester of melting point 107°–109° C crystallises out.

EXAMPLE 15

Analogously to the description in Example 2, 4.7 g of 5-benzoyl-6-methoxy-indane-1-carboxylic acid methyl ester and 20 ml of N sodium hydroxide solution in 50 ml of methanol give 5-benzoyl-6-methoxy-indane-1-carboxylic acid of melting point 126°–128° C (from ether-petroleum ether).

EXAMPLE 16

0.45 g of paraformaldehyde and 0.4 ml of benzyl-trimethyl-ammonium hydroxide (40% strength in methanol) are added to a solution of 3.0 g of 5-benzoyl-6-hydroxy-indane-1-carboxylic acid methyl ester in 20 ml of absolute dimethylsulphoxide, and the mixture is stirred for 3 hours at 80° C, whilst excluding moisture. It is then allowed to cool to room temperature, 100 g of ice are added to the reaction mixture, the pH is adjusted to 7 with acetic acid and the mixture is extracted with 3 times 50 ml of ether. The organic phases are combined, washed until neutral, dried over sodium sulphate and evaporated to dryness in vacuo. This gives 1-hydroxymethyl-5-benzyl-6-hydroxy-indane-1-carboxylic acid methyl ester in the form of a yellow oil (IR spectrum in $CH_2Cl_2$: $\nu_{OH}$: 3,600 cm$^{-1}$, $\nu_{C=O}$: 1,725 cm$^{-1}$).

EXAMPLE 17

A solution of 2.8 g of 1-hydroxymethyl-5-benzoyl-6-hydroxy-indane-1carboxylic acid methyl ester in 12 ml of 2 N sodium hydroxide solution and 50 ml of methanol is heated to the reflux temperature for 5 hours. It is then evaporated in vacuo to a volume of approx. 10 ml and the evaporation residue is partitioned between twice 50 ml of water and 50 ml of ether. The aqueous phases are combined, acidifed to pH 1 with concentrated hydrochloric acid and extracted with twice 50 ml of ether. The organic extracts are washed until neutral, dried over sodium sulphate and evaporated to dryness in vacuo. Chromatography of the evaporation residue on 100 g of silica gel using ether as the eluting agent gives pure 1-hydroxymethyl-5-benzoyl-6-hydroxy-indane-1-carboxylic acid in the form of yellow crystals of melting point 104°–110° C.

EXAMPLE 18

18 g of finely powdered aluminum chloride are added in portions of a solution of 8 g of indane-1-carboxylic acid methyl ester and 8.2 g of benzoyl chloride in 100 ml of carbon disulphide, whilst stirring in an anhydrous atmosphere. After completion of the addition, the reaction mixture is heated for 2 hours to the reflux temperature. It is then allowed to cool to room temperature, poured onto a mixture of 100 g of ice and 50 ml of concentrated hydrochloric acid and extracted with twice 100 ml of ether. The organic phases are combined, washed with twice 100 ml of water, dried over sodium sulphate and evaporated in vacuo. Distillation of the evaporation residue in a high vacuum gives 6-benzoyl-indane-1-carboxylic acid methyl ester in the fraction boiling at 165°–170° C (0.5 mm).

EXAMPLE 19

Analogously to the description in Example 2, 13 g of 6-benzoyl-indane-1-carboxylic acid methyl ester and 75 ml of 2 N sodium hydroxide solution in 500 ml of methanol give 6-benzoyl-indane-1-carboxylic acid of boiling point 200° C/0.04 mm Hg as a yellowish, viscous oil.

EXAMPLE 20

Dry ammonia is passed into a solution of 27 g of crude 5-benzoyl-6-acetoxy-indane-1-carboxylic acid chloride in 200 ml of anhydrous benzene at a temperature of 15°–20° C, with exclusion of moisture, until saturation is reached. The reaction solution is then evaporated to dryness in vacuo and the evaporation residue is partitioned between 200 ml of water and 3 times 200 ml of methylene chloride. The organic phases are washed until neutral, dried over sodium sulphate and evaporated in vacuo. Fractional crystallisation of the evaporation residue from hot dimethylformamide-water gives 5-benzoyl-6-hydroxy-indane-1-carboxylic acid amide of melting point 205°–207° C. The starting material can be obtained as follows. A solution of 20 g of 5-benzoyl-6-hydroxy-indane-1-carboxylic acid in 200 ml of acetic anhydride is heated to the reflux temperature for 4 hours. It is then evaporated to dryness in vacuo, 50 ml of toluene are added to the evaporation residue and the mixture is evaporated to dryness. This procedure is repeated twice more. The crude 5-benzoyl-6-acetoxy-indane-1-carboxylic acid thus obtained is used directly for further conversion.

20 ml of oxalyl chloride are added to a solution of the crude product, obtained as above, in 200 ml of anhydrous benzene at 0° C and the mixture is left to stand overnight at room temperature, with exclusion of water. It is then evaporated to dryness in vacuo. In order to remove the excess oxalyl chloride completely, 50 ml of absolute benzene are added and the mixture is evaporated to dryness in vacuo. This procedure is repeated twice. The crude 5-benzoyl-6-acetoxyindane-1-carboxylic acid chloride which remains in the evaporation residue is used directly for further conversion.

EXAMPLE 21

Analogously to the description in Example 2, 10 g of a mixture of 5-benzoyl- and 6-benzoyl-indane-1-acetic acid methyl ester and 30 ml of 2 N sodium hydroxide solution in 300 ml of methanol give 5-benzoyl- or 6-benzoyl-indane-1-acetic acid of melting point 133°–135° C (from ether-petroleum ether).

The starting material is obtained as follows:

22.9 g of finely powdered aluminium chloride are added in portions to a solution of 10.8 g of benzoyl chloride and 11.25 g of indane-1-acetic acid methyl ester in 120 ml of absolute carbon disulphide, whilst stirring in an anhydrous atmosphere. After completion of the addition, stirring is continued for 1 hour at room temperature. The reaction mixture is then poured onto 500 g of ice and extracted with twice 150 ml of ether. The organic phases are washed with water, dried over sodium sulphate and evaporated in vacuo. Distillation of the evaporation residue in a high vacuum gives a mixture of 5- and 6-benzoyl-indane-1-carboxylic acid methyl ester in the fraction boiling at 165°–170° C (0.04 mm).

EXAMPLE 22

Analogously to the description in Example 1, 6 g of 6-methoxy-indane-1-acetic acid methyl ester and 11.5 g of benzoyl chloride give 5-benzoyl-6-hydroxy-indane-1-acetic acid methyl ester of boiling point 180°–185° C/0.04 mm Hg (yellow oil).

EXAMPLE 23

Analogously to the description in Example 2, 7.5 g of 5-benzoyl-6-hydroxy-indane-1-acetic acid methyl ester and 50 ml of 2 N sodium hydroxide solution in 300 ml of methanol give 5-benzoyl-6-hydroxy-indane-1-acetic acid of melting point 148°–150° C (from ether-petroleum ether).

EXAMPLE 24

0.5 ml of concentrated sulphuric acid is added to a solution of 1.4 g of 5-benzoyl-6-hydroxy-indane-1-acetic acid in 300 ml of absolute methanol and the mixture is heated to the reflux temperature for 8 hours, with exclusion of water. The reaction mixture is then evaporated in vacuo to a volume of 5 ml and partitioned between 20 ml of water and twice 20 ml of ether. The organic phases are combined, washed until neutral, dried over sodium sulphate and evaporated in vacuo. Distillation of the evaporation residue in a high vacuum gives, in the fraction boiling at 180° C/0.04 mm, 5-benzoyl-6-hydroxyindane-1-acetic acid methyl ester as a yellow oil which is identical with the product described in Example 22.

EXAMPLE 25

26.6 g of finely powdered aluminium chloride are added in portions to a solution of 10 g of 6-methoxy-1,2,3,4-tetrahydro-1-naphthyl-acetic acid ethyl ester in 50 ml of absolute methylene chloride whilst stirring at 5° C, and thereafter 16.9 g of benzoyl chloride are added sufficiently slowly that the reaction solution boils gently under reflux. After completion of the addition, the reaction mixture is allowed to boil for a further 30 minutes and is then allowed to cool to room temperature, after which it is poured onto 300 g of ice. The mixture is extracted with 3 times 100 ml of methylene chloride and the organic phases are washed until neutral, dried over sodium sulphate and evaporated to dryness in vacuo. Chromatography of the evaporation residue on 500 g of silica gel, using methylene chloride as the eluting agent, gives 6-hydroxy-7-benzoyl-1,2,3,4-tetrahydro-1-naphthylacetic acid ethyl ester of boiling point 190° C/0.04 mm Hg.

EXAMPLE 26

Analogously to the description in Example 2, 5.5 g of 6-hydroxy-7-benzoyl-1,2,3,4-tetrahydro-naphthalene-acetic acid ethyl ester and 20 ml of 2 N sodium hydroxide solution in 250 ml of ethanol give 6-hydroxy-7-benzoyl-1,2,3,4-tetrahydro-1-naphthylacetic acid in the form of yellow crystals of melting point 118°–120° C (from ether-petroleum ether).

EXAMPLE 27

A solution of 2.36 g of 5-benzoyl-6-hydroxy-indane-1-carboxylic acid methyl ester in 6 ml of absolute tetrahydrofurane is added over the course of 30 minutes to a suspension of 440 mg of sodium hydride (58% strength in mineral oil) in 6 ml of absolute tetrahydrofurane, in a nitrogen atmosphere, whilst stirring; a vigorous evolution of gas occurs. After completion of the addition, a further 440 mg of sodium hydride (58% strength in mineral oil) and 1 ml of methyl iodide are added and stirring is continued for 30 minutes at 40° C. The reaction mixture is then cautiously poured onto 50 g of ice and extracted with twice 50 ml of chloroform. The organic phases are combined, washed successively with cold saturated sodium bicarbonate solution and with water, dried over sodium sulphate and evaporated in vacuo. Chromatography of the evaporation residue on 30 g of silica gel, using benzene-ethyl acetate (10:1) as the eluting agent, gives 1-methyl-5-benzoyl-6-methoxy-indane-1-carboxylic acid methyl ester as a colourless oil (mass spectrum: M$^+$: 324).

EXAMPLE 28

Analogously to the description in Example 2, 0.4 g of 1-methyl-5-benzoyl-6-methoxy-indane-1-carboxylic acid methyl ester and 5 ml of 2 N sodium hydroxide solution in 15 ml of methanol give 1-methyl-5-benzoyl-6-methoxy-indane-1-carboxylic acid of melting point 135°–137° C (from ether-petroleum ether). The starting material can be obtained as follows:

EXAMPLE 29

With stirring, 6 ml of dimethyl sulphide are added at 0° C in an atmosphere of nitrogen to a suspension of 8.05 g of N-chlorosuccinimide in 200 ml of absolute toluene and then at −25° C a solution of 12 g of crude 5-hydroxymethylphenyl-6-methoxy-indane-1-carboxylic acid methyl ester in 50 ml of absolute toluene is added. Upon completion of the addition, the mixture is further stirred for 90 minutes at −25° C. Then 8.3 ml of triethylamine are added to the reaction solution, which is stirred for a further 5 minutes and partitioned between 2 × 100 ml of 2 normal hydrochloric acid and 2 × 100 ml of ether. The organic phases are washed neutral, dried over sodium sulphate and evaporated to dryness in vacuo. The residue is chromatographed on silica gel with methylene chloride as eluant to yield 5-benzoyl-6-methoxy-indane-1-carboxylic acid methyl ester.

The starting material can be obtained as follows:

With stirring, 90 ml of titanium tetrachloride are added dropwise at 0° C in an inert atmosphere to a solution of 103 g of 6-methoxy-indane-1-carboxylic acid methyl ester in 500 ml of methylene chloride and then a solution of 60 g of dichloromethyl-methyl ether in 100 ml of absolute methylene chloride is added over the course of 30 minutes. Stirring is subsequently continued for 40 minutes at 0° C and then for 60 minutes at room temperature. The reaction mixture is then poured onto 1 kg of ice and extraction is performed with 5 × 100 ml of water. The organic phase is dried over sodium sulphate and evaporated in vacuo. Distillation of the residue yields in the fraction which boils at 180° C (0.09 mm Hg) a mixture of 5- and 7-formyl-6-methoxy-indane-1-carboxylic acid methyl ester, which can be resolved by fractional crystallisation from ether/methylene chloride/pentane or by chromatography on silica gel with methylene chloride as eluant. The 5-formyl-6-methoxy-indane-1-carboxylic acid methyl ester salts at 82° – 84° C.

With stirring, a solution of 15.7 g of bromobenzene in 100 ml of absolute tetrahydrofuran is added slowly dropwise in an atmosphere of nitrogen to 2.4 g of magnesium chips which are covered with a small amount of absolute tetrahydrofuran. Upon completion of the addition, stirring is continued for 1 hour at 40° C. The reaction mixture is then cooled to room temperature, conveyed to a drip funnel and added slowly dropwise with stirring in an inert atmosphere at −10° C to 23 g of 5-formyl-6-methoxy-indane-1-carboxylic acid methyl ester in 150 ml of absolute tetrahydrofuran. Upon completion of the addition, stirring is continued for 1 hour at 0° C and overnight at room temperature. The reaction solution is then poured into 200 ml of a saturated aqueous ammonium chloride solution and extraction is performed with 2 × 500 ml of methylene chloride. The organic phases are washed neutral, dried over sodium sulphate, treated twice with activated charcoal and evaporated in vacuo. The crude 5-hydroxymethylphenyl-6-methoxy-indane-1-carboxylic acid methyl ester (diastereoisomer mixture) is further processed direct without additional purification.

EXAMPLE 30

5 g of finely powdered sodium hydroxide are added to 5 g of 5-benzoyl-6-hydroxy-indane-1-carboxylic acid nitrile in 50 ml of ethylene glycol and the mixture is heated with stirring for 18 hours to 160° C in an inert atmosphere. The reaction mixture is then cooled to room temperature, poured into 100 g of ice water and extraction is performed with 2 × 100 ml of ether. The aqueous phase is adjusted to a pH of 2 with concentrated hydrochloric acid and extraction is performed with 2 × 100 ml of chloroform. The organic phases are washed neutral, dried over sodium sulphate and evaporated to dryness. Fractionally crystallisation from ethanol yields 5-benzoyl-6-hydroxy-indane-1-carboxylic acid (m.p. 185°- 187° C).

The starting material can be obtained as follows:

10 ml of phosphoroxy chloride are added to 1.0 of 5-benzoyl-6-hydroxy-indane-1-carboxylic acid amide and the mixture is heated to 60° C under anhydrous conditions. The reaction mixture is then evaporated to dryness and the residue is partitioned between 2 × 200 ml of methylene chloride and 20 ml of water. The organic phases are washed neutral, dried over sodium sulphate and evaporated in vacuo. Crystallisation of the residue from ether/petroleum ether yields the 5-benzoyl-6-hydroxy-indane-1-carboxylic acid nitrile, which melts at 90°- 91° C (yellow flakes).

EXAMPLE 31

Tablets, containing 100 mg of active substance are prepared in the usual manner to have the following composition:

| Composition: | |
|---|---|
| 5-Benzoyl-6-hydroxy-indane-1-carboxylic acid | 100 mg |
| Wheat starch | 73 mg |
| Lactose | 50 mg |
| Colloidal silica | 13 mg |
| Talc | 12 mg |
| Magnesium stearate | 2 mg |
| | 250 mg |

Preparation

The 5-benzoyl-6-hydroxy-indane-1-carboxylic acid is mixed with a part of the wheat starch, with lactose and with colloidal silica and the mixture is forced through a sieve. A further part of the wheat starch is worked into a paste with a 5-fold amount of water on a waterbath and the powder mixture is kneaded with this paste until a slightly plastic mass has been produced.

The plastic mass is forced through a sieve of approx. 3 mm mesh width and dried and the resulting dry granules are again forced through a sieve. The remaining wheat starch, talc and magnesium stearate are then added to the mixture and the mixture is pressed to give tablets weighing 250 mg and having a breaking groove.

We claim:

1. A compound of the general formula

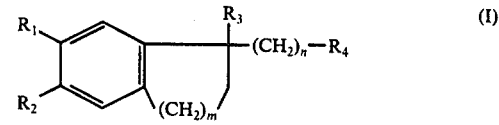

wherein one of the two radicals $R_1$ and $R_2$ denotes benzoyl, or benzoyl substituted by at least one member selected from lower alkyl, lower alkoxy, halogen and trifluoromethyl, and the other denotes hydrogen, hydroxy, hydroxy esterified by a lower alkanecarboxylic acid, or hydroxy etherified by a lower alkanol, $R_3$ denotes hydrogen, lower alkyl or lower hydroxyalkyl, $R_4$ denotes carboxyl, or carboxyl esterified by a lower alkanol or a lower alkanol which is substituted by hydroxy or lower alkoxy, $m$ denotes 1 or 2 and $n$ denotes 0 or 1, therapeutically acceptable salts of said carboxyl compounds.

2. A compound as claimed in claim 1, of the general formula I, wherein one of the two radicals $R_1$ and $R_2$ denotes benzoyl, or benzoyl substituted by a member selected from lower alkyl, lower alkoxy, halogen and trifluoromethyl, and the other denotes hydrogen, hydroxy, hydroxy esterified by a lower alkanecarboxylic acid, or hydroxy etherified by a lower alkanol, in each case with up to 7 carbon atoms, $R_3$ denotes hydrogen, lower alkyl or α-hydroxy-lower alkyl each with up to 4 carbon atoms, $R_4$ denotes carboxyl, or carboxyl esterified by a lower alkanol, or a lower alkanol substituted by lower alkoxy or by hydroxy, $n$ is 0 or 1 and $m$ denotes 1 or 2.

3. A compound as claimed in claim 1, of the general formula I, wherein one of the two radicals $R_1$ and $R_2$ denotes benzoyl, or benzoyl substituted by a member selected from lower alkyl, lower alkoxy, halogen and trifluoromethyl, and the other denotes hydrogen, hydroxy, or hydroxy esterified by a lower alkanecarboxylic acid with 2 to 4 carbon atoms, or hydroxy esterified by a lower alkanol with 1 to 4 carbon atoms, $R_3$ denotes hydrogen or lower alkyl with up to 4 carbon atoms, $R_4$ denotes carboxyl, or carboxyl esterified by a lower alkanol, or a lower alkanol substituted by lower alkoxy or by hydroxy, $n$ is 0 or 1 and $m$ is 1.

4. A compound as claimed in claim 1, of the general formula I, wherein one of the radicals $R_1$ and $R_2$ denotes benzoyl and the other denotes hydroxyl, $R_3$ denotes hydrogen, $R_4$ denotes carboxyl, or carboxyl esterified by a lower alkanol with 1-4 carbon atoms, $n$ is 0 and $m$ is 1.

5. A compound as claimed in claim 1 of the general formula I, wherein one of the radicals $R_1$ and $R_2$ denotes benzoyl, or benzoyl mono-substituted by lower alkyl or lower alkoxy with up to 4 carbon atoms, trifluoromethyl or halogen and the other denotes hydroxy, $R_3$ denotes hydrogen, $R_4$ denotes carboxyl, or carboxyl esterified by a lower alkanol with 1–4 carbon atoms, $n$ is 0 and $m$ is 1.

6. A compound as claimed in claim 1 being 5-benzoyl-6-hydroxyindane-1-carboxylic acid methyl ester.

7. A compound as claimed in claim 1 being 5-benzoyl-6-hydroxy-indane-1-carboxylic acid or a therapeutically acceptable salt thereof.

8. A compound as claimed in claim 1 being 5-benzoyl-6-hydroxyindane-1-carboxylic acid n-butyl ester.

9. A compound as claimed in claim 1 being 5-benzoyl-6-hydroxyindane-1-carboxylic acid ethyl ester.

10. A compound as claimed in claim 1 being 5-(p-chlorobenzoyl)-6-hydroxy-indane-1-carboxylic acid or a therapeutically acceptable salt thereof.

11. A compound as claimed in claim 1 being 5-(o-chlorobenzoyl)6-hydroxy-indane-1-carboxylic acid or a therapeutically acceptable salt thereof.

* * * * *